United States Patent [19]
Brown et al.

[11] Patent Number: 5,844,151
[45] Date of Patent: Dec. 1, 1998

[54] METHOD AND APPARATUS FOR DETECTING AND MEASURING ORGANIC MATERIALS ON COMPONENTS OF A MAGNETIC STORAGE SYSTEM

[75] Inventors: Charles Allan Brown, Los Gatos; Ronald Louis Herbold, Fremont; Andrew Marian Homola; Heidi Lee Merkins, both of Morgan Hills; Herman Russell Wendt, San Jose, all of Calif.

[73] Assignee: International Business Machines Corporation, Armonk, N.Y.

[21] Appl. No.: 846,407

[22] Filed: Apr. 30, 1997

[51] Int. Cl.$^6$ .................................................... G01N 25/14
[52] U.S. Cl. .............................. 73/866; 374/45; 73/865.9
[58] Field of Search .................................. 73/866, 865.9; 374/45, 57; 436/2, 5, 147

[56] References Cited

U.S. PATENT DOCUMENTS

| | | | |
|---|---|---|---|
| 3,998,101 | 12/1976 | Bradshaw et al. | 73/864 |
| 4,858,767 | 8/1989 | Myers et al. | 73/863.92 X |
| 4,995,273 | 2/1991 | Kisima et al. | 374/57 X |
| 5,177,995 | 1/1993 | Risch et al. | 73/23.41 |
| 5,181,428 | 1/1993 | Chriswell | 73/866 X |
| 5,209,130 | 5/1993 | Ohsaki et al. | 73/866 |
| 5,285,064 | 2/1994 | Willoughby | 250/288 |

FOREIGN PATENT DOCUMENTS

| | | | |
|---|---|---|---|
| 287140 | 11/1990 | Japan | 73/866 |
| 6438 | 1/1991 | Japan | 73/866 |
| 547687 | 2/1977 | U.S.S.R. | 374/45 |
| 1290152A | 2/1987 | U.S.S.R. | 422/101 |
| 1370565 | 1/1988 | U.S.S.R. | 73/866 |

OTHER PUBLICATIONS

*Patent Abstracts of Japan* GP p. 1301, vol. 16, No. 24 Abs Pub date Jan. 21, 1992 (03–237674) "Magnetic Disk Device" Bunji Ishida.

*Primary Examiner*—Thomas P. Noland
*Attorney, Agent, or Firm*—Noreen A. Krall; Robert B. Martin

[57] ABSTRACT

A method and apparatus for detecting and measuring organic materials present on components used in magnetic storage systems, such as an actuator coil. The component is heated on a hot plate, and a concave lens with a low surface energy coating is placed over the component. The contaminants volatilize and condense on the glass lens. The condensate is collected in solvent. The solvent is evaporated and the size of the residue is measured. A determination can be made whether the component is suitable for used in a magnetic storage system.

14 Claims, 9 Drawing Sheets

METHOD AND APPARATUS FOR DETECTING AND MEASURING ORGANIC MATERIALS ON COMPONENTS OF A MAGNETIC STORAGE SYSTEM

BACKGROUND OF THE INVENTION

1. Field of the Invention

The present invention relates generally to magnetic storage systems, and in particular to a method and apparatus for detecting and measuring organic materials on components such as actuator coils for magnetic storage systems before the components are used in the system.

2. Description of the Related Art

Magnetic storage systems are information storage devices which utilize at least one rotatable magnetic disk having concentric data tracks defined for storing data, a magnetic recording head or transducer for reading data from and writing data to the various data tracks, a slider for supporting the transducer adjacent the data tracks typically in a flying mode above the storage media, a suspension assembly for resiliently supporting the slider and the transducer over the data tracks, and a positioning actuator coupled to the transducer/slider/suspension combination for moving the transducer across the media to the desired track and maintaining the transducer over the data track centerline during a read or a write operation. The transducer is attached to or is formed integrally with the slider which supports the transducer above the data surface of the storage disk by a cushion of air, referred to as an air bearing, generated by the rotating disk.

Alternatively, the transducer may operate in contact with the surface of the disk. Thus, the suspension provides the desired slider loading and dimensional stability between the slider and an actuator arm which couples the transducer/slider/suspension assembly to the actuator. The actuator positions the transducer over the correct track according to the data desired on a read operation or the correct track for placement of the data during a write operation. The actuator is controlled to position the transducer over the desired data track by shifting the combination assembly across the surface of the disk in a direction generally transverse to the data tracks. The actuator may include a single arm extending from a pivot point, or alternatively a plurality of arms arranged in a comb-like fashion extending from a pivot point. A rotary voice coil motor (vcm) is attached to the rear portion of the actuator arm or arms to power movement of the actuator over the disks.

The vcm located at the rear portion of the actuator arm is comprised of a top plate spaced above a bottom plate with a magnet or pair of magnets therebetween. The vcm further includes an electrically conductive coil disposed within the rearward extension of the actuator arm and between the top and bottom plates, while overlying the magnet in a plane parallel to the magnet. In operation, current passes through the coil and interacts with the magnetic field of the magnet so as to rotate the actuator arm around its pivot point and thus positioning the transducer as desired.

The magnetic media disk or disks in the magnetic storage system are mounted on a spindle. The spindle is attached to a spindle motor which rotates the spindle and the disks to provide read/write access to the various portions on the concentric tracks on the disks. The spindle motor contains conductive coils in the spindle motor windings.

During manufacturing processes, the components previously mentioned, such as the actuator coil or the spindle motor windings, are exposed to and often treated with organic materials such as adhesives and lubricants which can be harmful to the operational environment of the magnetic storage system. The organic materials may include the wire lubricants on the actuator coils or spindle motor windings, or alternatively be the adhesives during winding or finishes on the components. This exposure is further subject to lot to lot variations. These materials can be problematic during operation of the disk drive system under normal file operating systems. In one such example, when the disk drive is in operation, power is supplied to the actuator coil. This causes the coil to get hot. Organic materials present on the coil volatilizes to generate a vapor inside the disk drive system. The vapor migrates from the actuator assembly where the temperature is hot and condenses upon the surface of the disk where the temperature is significantly cooler than in the actuator assembly. The same process could be described in connection with the operation of the spindle motor assembly.

This scenario presents problems for normal operation of the magnetic storage system because this vapor phase transport provides means for the contaminants to exit the coil and contaminate the surface of the disk. This, in turn, can cause file failure either by direct interference of the materials on the disk with the head flying during operation, or alternatively, by inducing stiction upon landing. Stiction is particularly problematic as requirements for smaller disk drives is controlling in the laptop or notebook industry. To accommodate the current capacity requirements of disk drives as well as meeting the size constraints of laptop or notebook markets, disks are being stacked very closely together with the expectation that they can be written to or read from within these very small spacings. Accordingly, extremely smooth surfaces exist on both the disk surface and the magnetic recording face of the slider attached to the load arm of the actuator. These extremely smooth surfaces are necessary to support the low fly height associated with high density recording. However, with the condensation of the lubricant coating from the coil onto the disk surface, the surface becomes chemically contaminated causing the problem of stiction in the drive. Stiction occurs as two very smooth surfaces stick to each other and effectively prevent the removal of one from the other. The stiction forces may be sufficient to prevent the rotation of the disk; but if the disk can be rotated, damage almost certainly will occur to the surface of the disk or slider due to the fact that the slider is in contact with and stuck to the disk surface as the disk moves relative to the slider. As stiction is a more recent problem plaguing the disk drive industry, there is currently no known solution to this problem.

To combat against this damage by condensation of these materials on the surface of the disk, one approach has been to introduce specific vacuum baking operations of the components into the manufacturing process to purge organics which can evolve at elevated temperatures. However, there has not been a way to monitor the effectiveness of these processes.

Various approaches have been considered in the prior art for addressing the effectiveness of the aforementioned process. These included a number of solvent based and specific detector based approaches. These however, did not meet the needs of a magnetic storage system engineer. Solvent extraction approaches were discarded as all systems tested extracted materials which were not volatile under even the most extreme file conditions. For example, very high molecular weight oils are easy to extract but pose no threat to the file. Solvent extract was discarded as an approach because it would lead to discarding perfectly satisfactory parts. Specific detectors was not an adequate approach because all tested were sensitive to both condensible and non condensible hydrocarbons. Furthermore, efforts to prefractionate the components produced highly variable and unreliable information. Depending upon conditions components would have passed with high loads of condensible organics or failed with low loads. Accordingly, it can be seen that there is a need to provide a method for measuring the effectiveness of the contaminant removal manufacturing processes. It can further be seen that it is desirable to provide a method and apparatus for detecting and measuring these materials from disk drive components prior to assembly in a magnetic storage systems. There is also a need for a method and apparatus for detecting and measuring these materials that is simple to administer and does add significant cost to the magnetic storage system assembly process.

For the foregoing reasons, it becomes necessary to engineer a new method of detection and measurement of organic materials on components prior to assembly into magnetic storage systems.

SUMMARY OF THE INVENTION

To overcome the shortcomings of the prior art, it is the object of the invention to provide a method for determining the effectiveness of the contaminant removal processes used in manufacturing disk drive components. It is the further object of the invention to provide a means to ensure that the file organic atmospheric burden remains within safe limits by monitoring certain disk drive components. It is also the object of the invention to provide a method of detection and measurement of these organic materials that is simple and cost efficient when incorporated into the magnetic storage system manufacturing process. Accordingly, the present invention provides a method and apparatus for detecting and measuring organic materials on components such as actuator coils, motor coils and gaskets for a magnetic storage systems. It is known in the magnetic storage system art that organic materials can evolve from these various system components such as coils and gaskets under normal file operating conditions. As previously described, those materials may vaporize during file operation and condense at the head/disk interface, which is usually cooler than at the source of the material. This event can cause a system failure either by direct interference with the head flying during operation or by inducing stiction upon landing. It is the object of the present invention to provide a method and apparatus to detect and minimize the presence of these condensible materials from disk drive components.

In accordance with the present invention, an apparatus is provided which is comprised of a collection chamber disposed above a heating source. In a preferred embodiment, the collection chamber includes a ring placed on a flat surface of a heating source or heat block, and a concave lens having a low energy surface placed over the ring. The disk drive component such as an actuator coil is placed within the ring, under the lens. Above the lens a cooling means is provided to create a temperature differential between the heating source and the lens.

In a preferred embodiment, the method of the present invention is comprised of the following steps. The drive component is placed on the surface of the heating source or heating block. A concave lens having a low energy surface is placed over the component, creating a collection chamber about the component. A coolant is placed over the lens. The heat source is heated to a temperature sufficient to cause any organic materials to vaporize from the component and condense on the surface of the lens. The lens is then removed from the heating source and the condensed material is collected. The condensed material is measured and a determination can be made whether the component or lot of components is acceptable for use in a magnetic storage system.

Although the preferred embodiment of the present invention is shown and described in connection with the coil found in the actuator assembly, it will be appreciated by those skilled in the art that the apparatus and method taught herein are also applicable to other disk drive components such as coil windings for spindle motors, solenoids, etc.

These and various other advantages and features of novelty which characterize the invention are pointed out with particularity in the claims annexed hereto and form a part hereof. However, for a better understanding of the invention, its advantages, and the objects obtained by its use, reference should be made to the drawings which form a part hereof, and to the accompanying descriptive matter, in which there is illustrated and described specific examples of an apparatus and method in accordance with the invention.

DESCRIPTION OF THE ILLUSTRATED EMBODIMENTS

The present description is described in a preferred embodiment in the following description with reference to the Figures, in which like numbers represent the same or similar elements. While this invention is described in terms of the best mode for achieving this invention's objectives, it will be appreciated by those skilled in the art that variations may be accomplished in view of these teachings without deviating from the spirit or scope of the invention.

Figure 1:
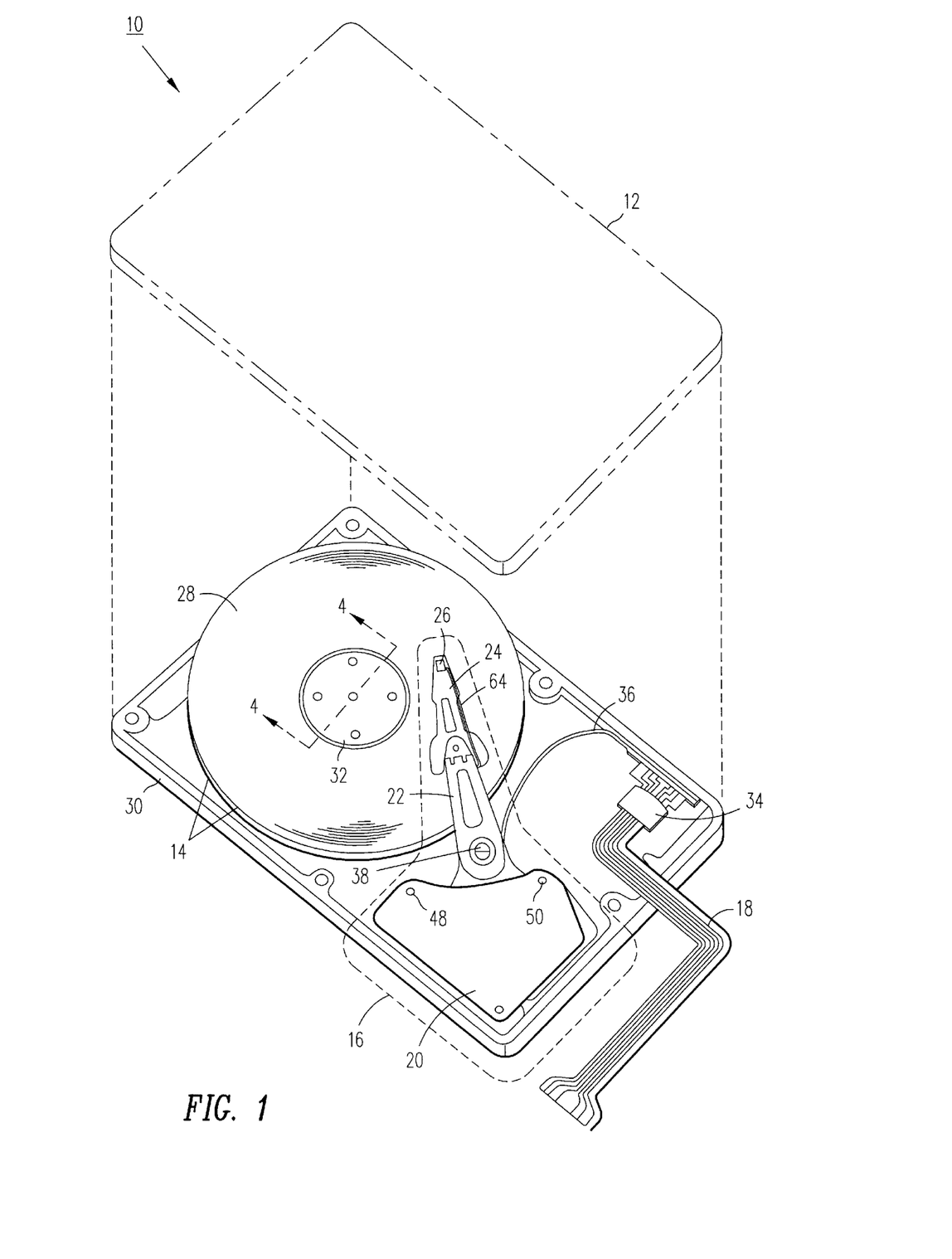
FIG. 1 illustrates a perspective view of a disk drive in accordance with the present invention showing the inside of the disk drive.

FIG. 1 shows a disk drive system, designated by the general reference number 10. The lid 12 of the disk drive is shown exploded and in phantom. In operation, the lid would be disposed atop of housing 30.

The disk drive comprises one or more magnetic disks 14. The disks 14 may be conventional particulate or thin film recording disks, which are capable of storing digital data in concentric tracks. In a preferred embodiment, both sides of the disks 14 are available for storage, and it will be recognized by one of ordinary skill in the art that the disk drive 10 may include any number of such disks 14.

The disks 14 are mounted to a spindle 32. The spindle 32 is attached to a spindle motor which rotates the spindle 32 and the disks 14 to provide read/write access to the various portions of the concentric tracks on the disks 14.

An actuator assembly 16 is indicated by the dashed lines in FIG. 1. The actuator assembly 16 includes a positioner arm 22, and a suspension assembly 24. The suspension assembly 24 includes a read/write head 26 at its distal end. Although only one read/write head 26 of the suspension assembly is shown, it will be recognized that the disk drive 10 has one read/write head for each side of each disk 14 included in the drive. The positioner arm 22 further comprises a pivot 38 around which the positioner arm 22 pivots.

The disk drive 10 further includes read/write chip 34. As is well known in the art, the read/write chip 34 cooperates with the read/write heads 26 to read data from and write data to the disks 14. A flexible printed circuit member 36 carries digital signals between the chip 34 and the actuator assembly 16. One or more electrical conductors 64 are routed along the pivot arm 22 and suspension 24 to carry electrical signals to and from the read/write head 26. A separate flexible printed circuit member 18 interfaces with the chip 34 and associated drive electronics (not shown).

A vcm top plate 20 is also shown in FIG. 1 and is part of the actuator assembly 16. One of the functions of the actuator assembly 16 is to move the positioner arm 22 around pivot 38. This specific operation is detailed below.

Figure 2:
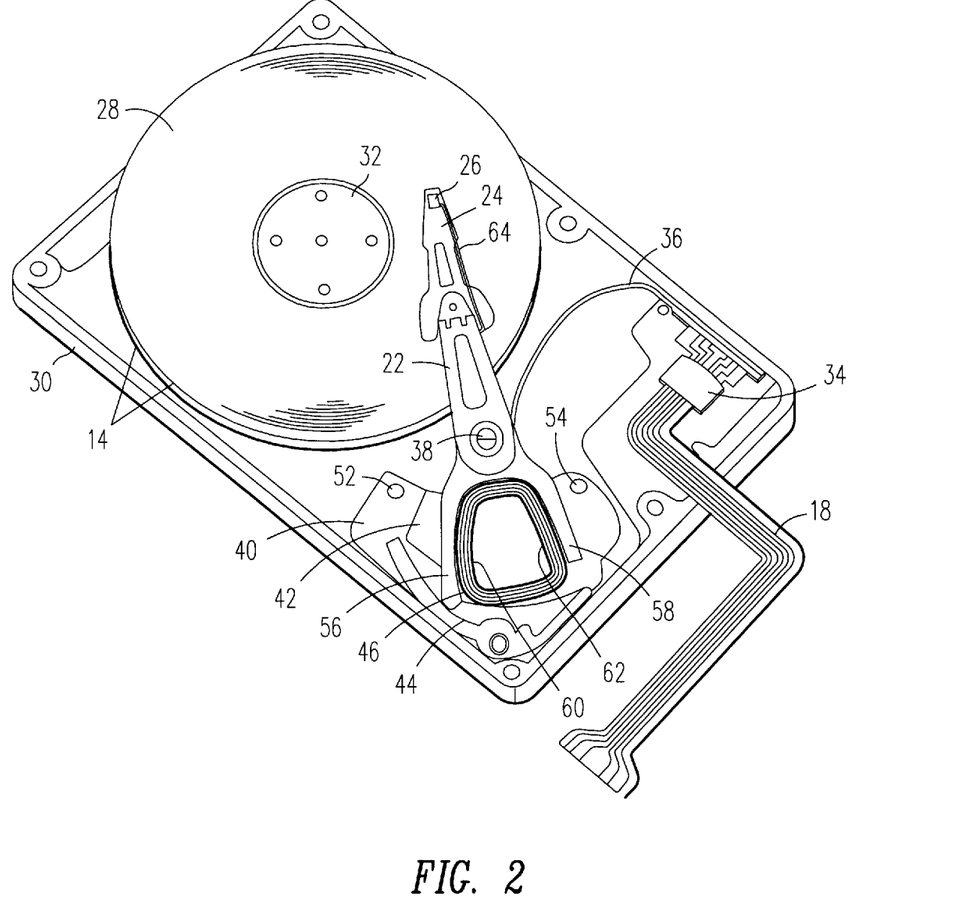
FIG. 2 illustrates a perspective view of a disk drive in accordance with the present invention, showing the inside of the disk drive with the top plate of the voice coil motor removed.

Referring now to FIG. 2, a perspective view of the disk drive 10 is shown with vcm top plate 20 removed to reveal the details of the remainder of the actuator assembly 16. The actuator assembly 16 further comprises a vcm bottom plate 40 and a magnet 42. It is understood that magnet 42 may be a single magnet or a pair of magnets. In operation, the vcm top plate 20 is spaced above the vcm bottom plate 40 and magnet 42. The actuator assembly 16 further includes a conductive coil 46, which is wound from a conductive material and overlies magnet 42 is a plane parallel to the magnet 42.

The vcm bottom plate 40, the magnet 42 and the vcm top plate 20, in combination with the conductive coil 46, substantially make up a voice coil motor (vcm) which acts to position the actuator assembly 16, as is well known in the art. Specifically, current passing through the coil 46 interacts with the magnetic field of the magnet 42, to rotate the positioner arm 22 and suspension assembly 24 around the pivot 38, thus positioning the read/write head 26 as desired. Also shown in FIG. 2 is a latching mechanism 44, known in the art, which serves to secure the position of the actuator assembly 16 when the drive 10 is not in operation.

Figure 3A:
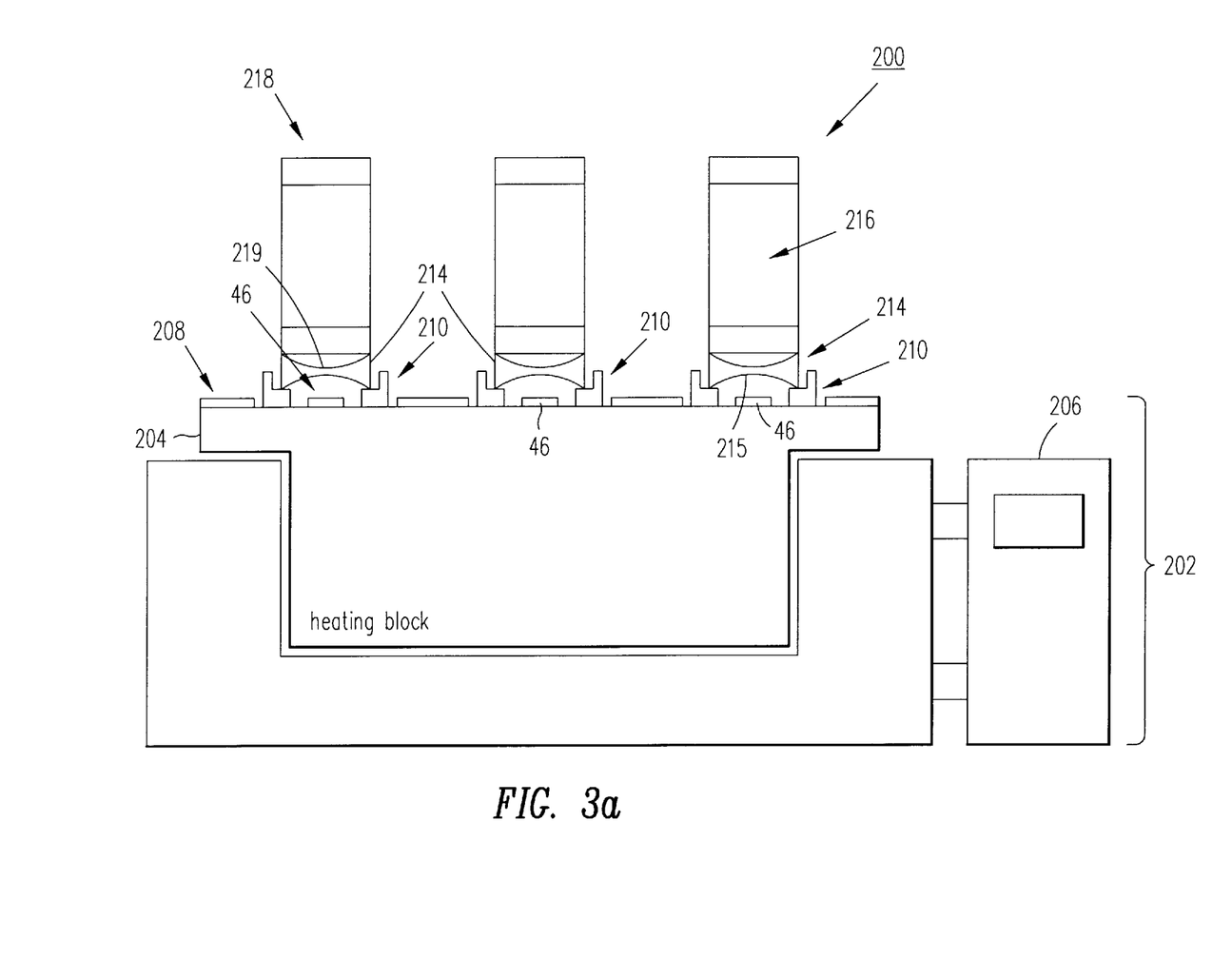
FIGS. 3a and 3b are simplified schematic block diagrams of the apparatus for collecting the organic materials in accordance with the present invention, illustrating different lens shapes and cooling means.
Figure 3B:
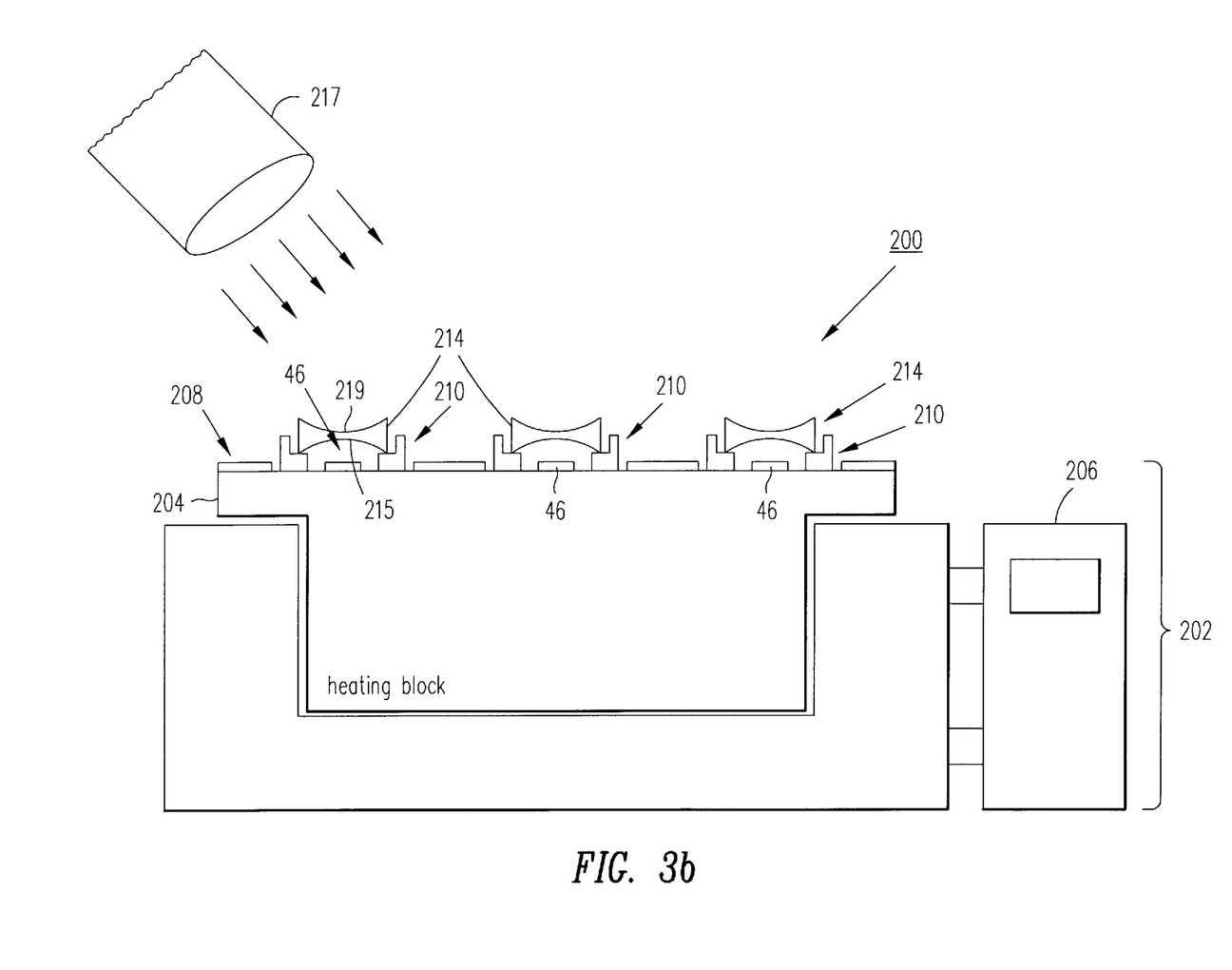
Figure 4:
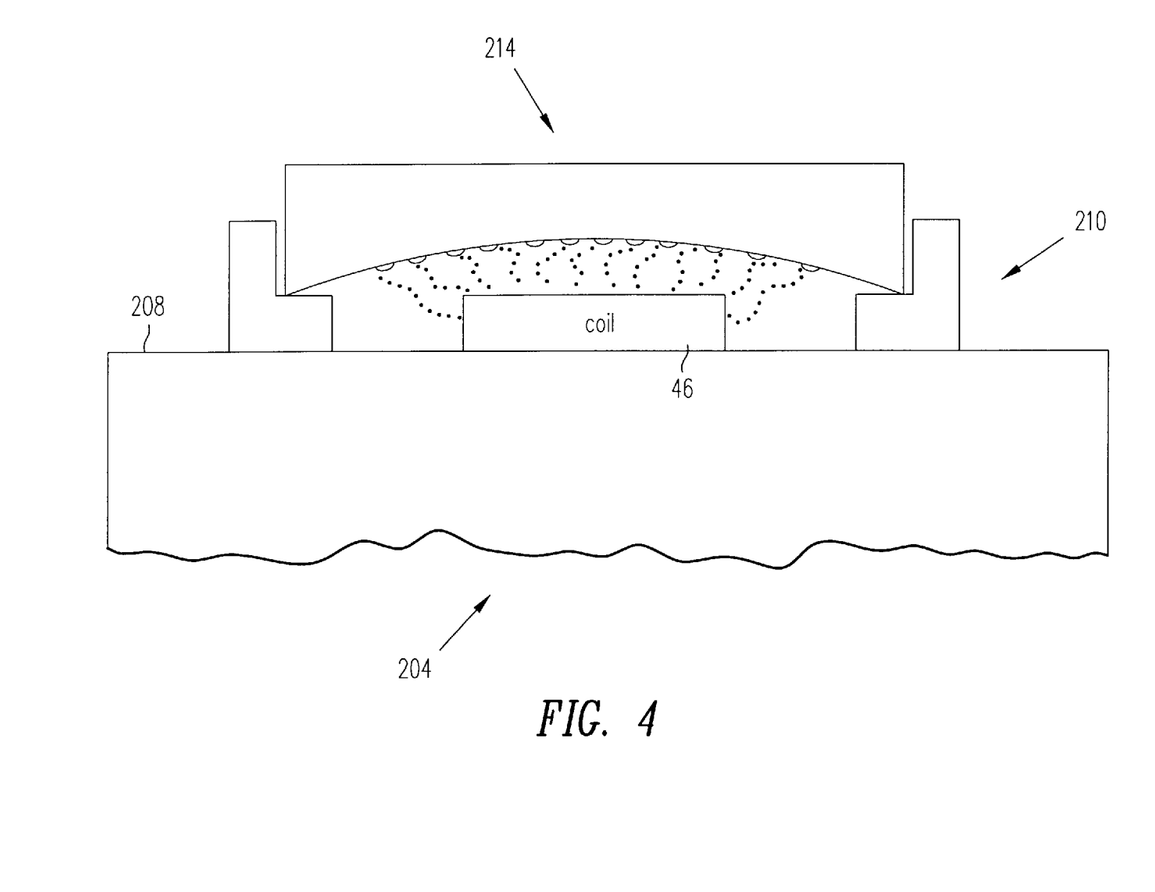
FIG. 4 is a simplified illustration of the method of collection in accordance with the present invention.

FIGS. 3a and 3b illustrate various embodiments of the collection apparatus 200 used in accordance with the present invention. As seen with reference to FIG. 3a, a heating source 202 is provided. Here the heating source 202 is comprised of a heating block 204 which is disposed within a heating unit 206. On the upper surface 208 of the heating block 204, one or more rings 210 are located. Placed upon the ring 210 is lens 214 having a low energy surface. The low energy surface may be through a coating process or semiconductor processes, as will subsequently be described. The ring 210 supports lens 214 above heat block 204. Lens 214 is preferably concave, and the curved portion 215 is positioned away from the heating source 202. In FIG. 3a, lens 214 is a concave/planar lens so that the planar outer side 219 can also contact and support the means for cooling the lens 214. In FIG. 3b, lens 214 is shown to be concave/concave, so that the concave outer side 219 acts as a basin towards which cool air can be focused. In both FIGS. 3a and 3b, the inner portion 215 of the lens is concave as this has been determined to be the most suited for the collection process that will be described below. However, lens may alternatively be a flat surface, which would simply inject an additional degree of care into the collection process.

With reference again to FIG. 3a, it can be seen that above the lens 214 is a located a coolant 216. Coolant 216 may be water or any liquid or solid suitable for keeping the temperature at the lens 214 lower than that of the heating source 202, and a cooling reservoir 218 may be provided above the coolant 216 to provide a continued temperature differential during continued or prolonged operation. In FIG. 3b, it can be seen that the means for cooling the lens may be a fan or focused air supply 217. It is understood that any suitable means for keeping the temperature at the lens 214 lower than at the surface of the heating block is within the scope of the invention described herein.

In accordance with the method of the present invention, a disk drive component such as an actuator coil 46, is placed directly on the heat source 202, or on any suitable heat transferring surface which is then placed on the heat source 202. The concave lens having a low energy surface 214 is placed over the component, such that its peripheral edge rests upon the heat source 202. In order to accommodate components of various sizes and dimensions, a ring 210 may be placed about the component on the heat source 202 and the lens 214 then placed on the ring 210 such that the peripheral edge of the lens 214 rests on the ring 210 rather than directly on the heat source 202. Ring 210 also provides additional distance between lens 214 and heat source 202 which helps maintain a temperature differential as will be described. A coolant 216 is placed above lens 214 in order to create a temperature differential between the heat source 202 and the lens 214. A cooling reservoir 218 may be provided above the coolant 216 to maintain the lower temperature at the lens 214. Next, the temperature of the heat source 202 is raised. The temperature is increased to the temperature necessary to cause any organic materials located on the coil 46 to volatize and subsequently condense on the surface of the lens 214.

The temperatures used in accordance with the heating step of the present method are selected on the basis of disk file experience and calibration against the Rochester Environmentally Accelerated Friction Tester (EAFT), which is presently the only recognized standard in this art. The heat block 204 temperature is raised to a temperature which is sufficiently above normal disk file 10 operating temperatures to accelerate the evolution of volatile materials to an extent approaching the entire expected disk file lifetime burden. This temperature, however, must be low enough not to risk decomposition of the actual drive components. The temperature at the coolant or condensation temperature is about 25±5 degrees Celsius, which is high enough to avoid condensation of relatively harmless low boiling solvents. It is sufficiently below the actual head/disk interface to allow some margin of safety for borderline condensibles.

Figures 5A, 5B:
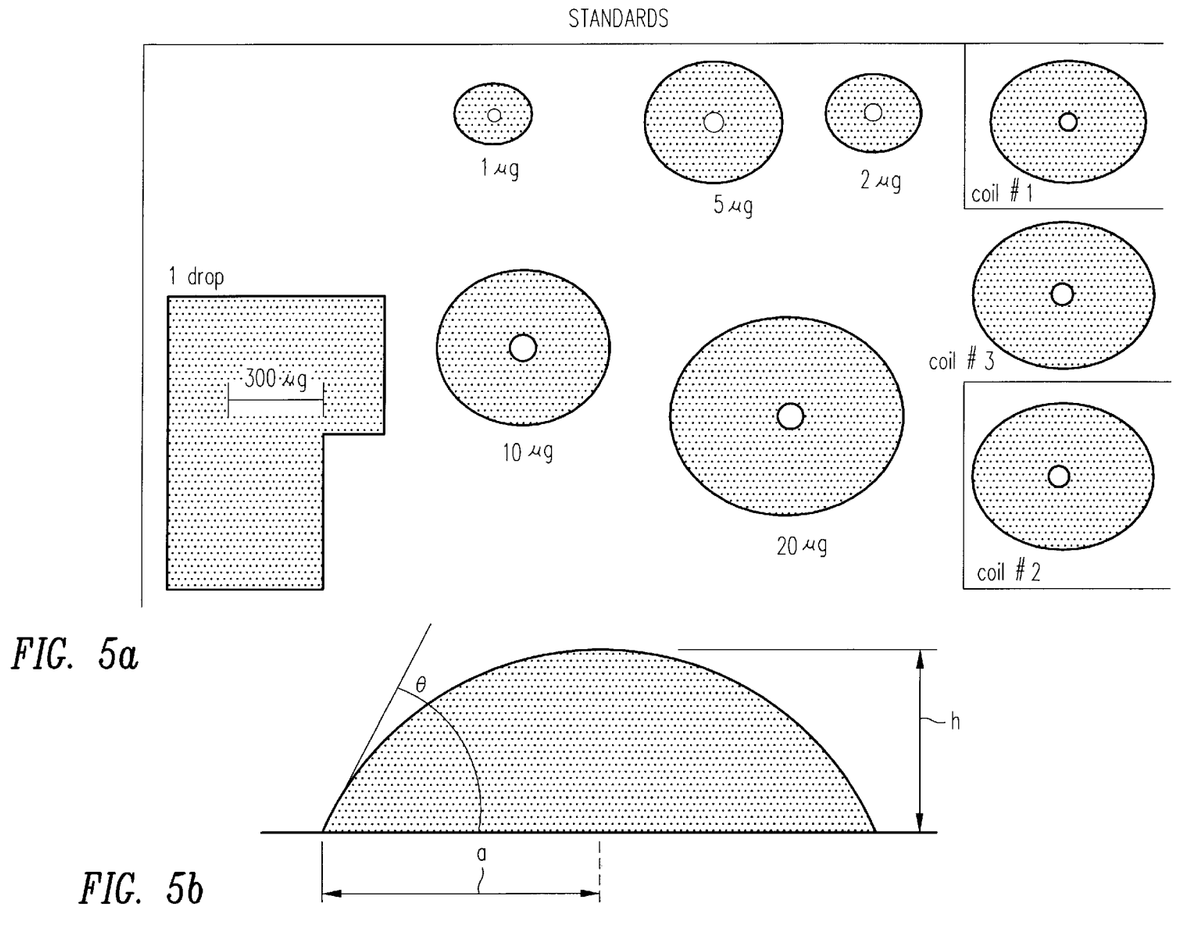
FIGS. 5a and 5b are illustrations of samples collected and measured in accordance with the present invention.
Figure 6A:
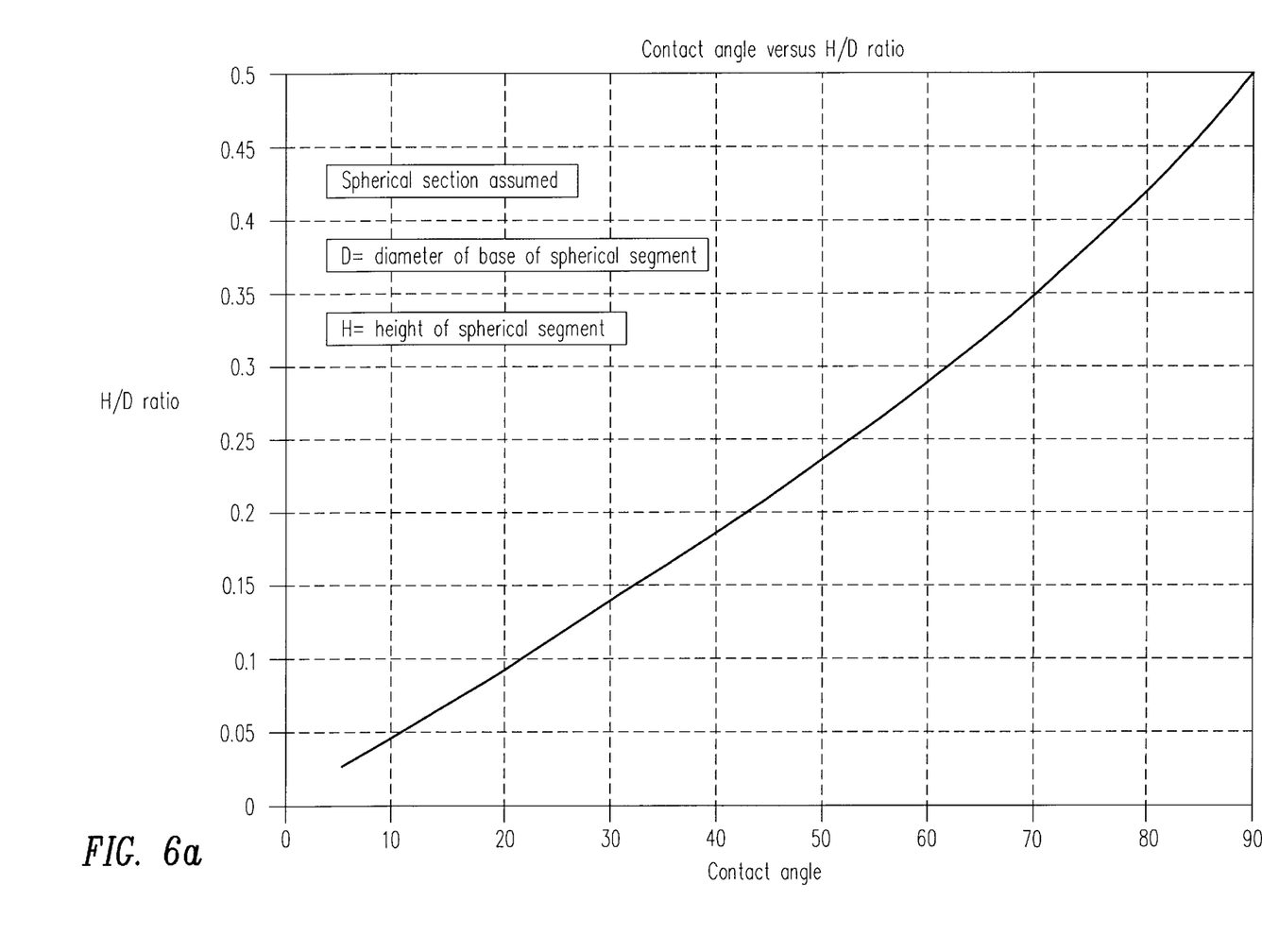
FIG. 6a illustrates the relationship between the contact angle of the spherical segment of the condensed material and the height to diameter ratio of the spherical segment of condensed material.
Figure 6B:
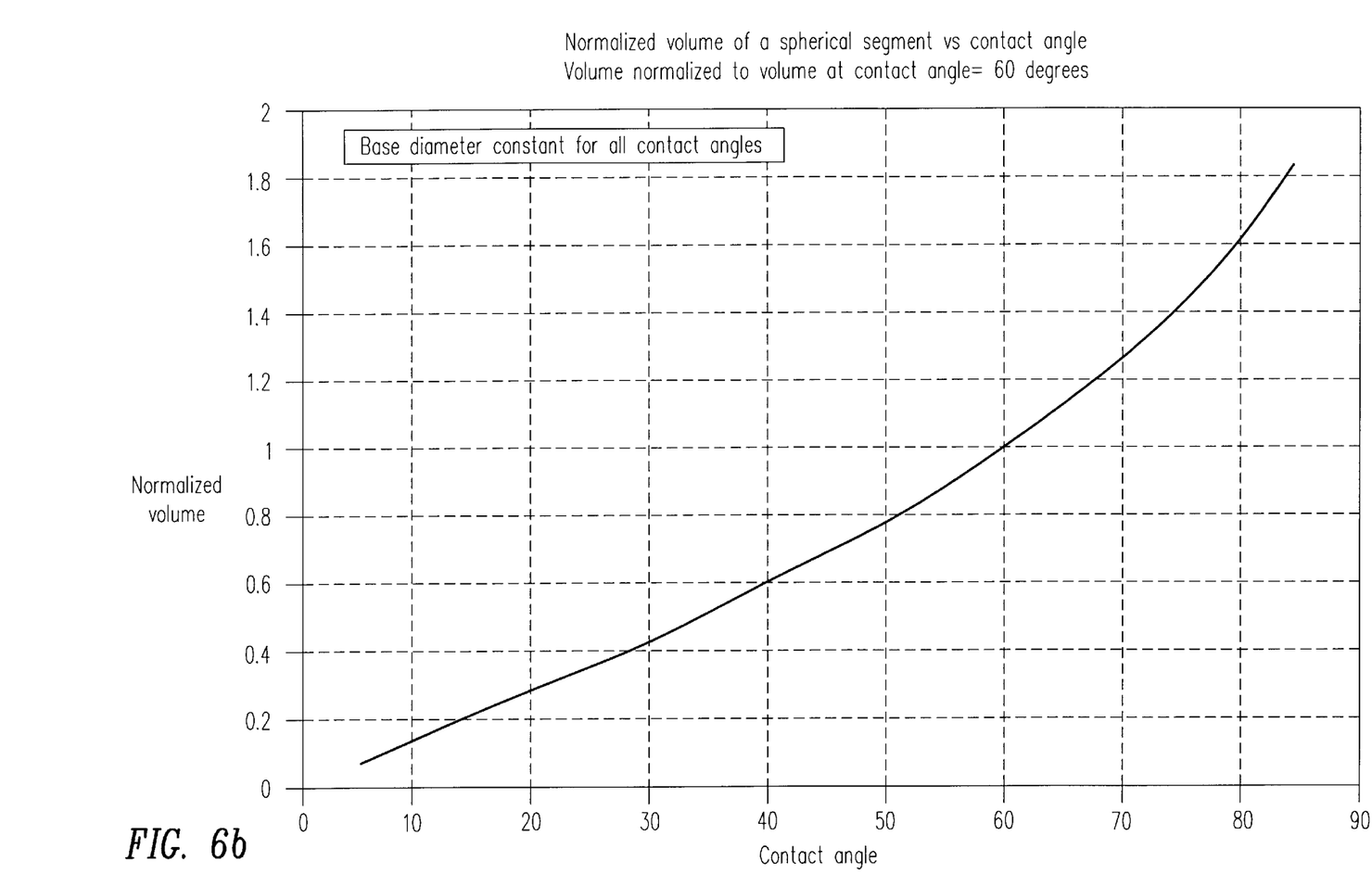
FIG. 6b illustrates the relationship between a specific contact angle and a normalized volume (at a contact angle= 60 degrees) of collected materials.
Figure 7:
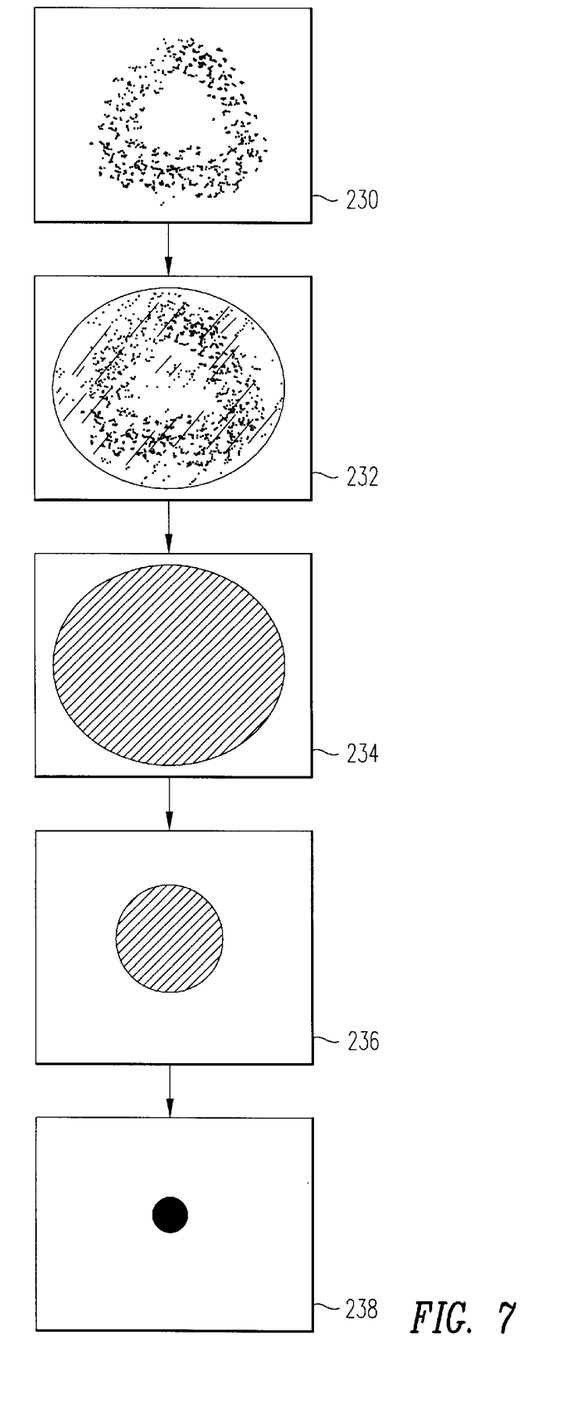
FIG. 7 is a flow diagram of the method of the present invention.

With reference to FIGS. 5 to 7, the method for collection and measuring of the condensed material from the lens 214 is described as follows. A solvent is dropped into the middle of the lens 214, and swirled over the surface until all of the deposited material is dissolved and collected into the solvent. The solvent selected for the collection step should be a volatile saturated hydrocarbon solvent such as hexane, cyclo-hexane or isooctane which has reasonable solvent powers to collect deposited materials but does not wet or dissolve the coating on the lens 214. Here, hexane is selected as the gathering solvent because of its high solvent power for most hydrocarbons, its volatility, its high commercial purity and low toxicity. For the purposes of collecting the condensed materials from a single actuator coil, 50 µl of the hexane solvent has been found to be optimum. The collection process is easily enhanced with the use of lateral illumination. The deposited material forms a haze on the lens which is gathered up in the hexane droplet by rolling the droplet in increasingly larger concentric circles. Examples of droplets collected are illustrated in FIG. 5*a*.

Next, after the evaporation of the solvent, the droplets are measured by placing the lens under a microscope. The droplets are centered under the 0–100 scale as viewed through the eyepiece. The diameter of the droplet is then measured with the reticule in the microscope eyepiece. The reticule range is from 0 to 100 units. The droplet should be reasonably round with little detectible distortion. The squalene standard may have a crystalline appearance inside the drop. The following is a simple formula used to calculate the mass of the droplet.

$$\text{Mass} = \rho(\pi h)(h^2 + 3a^2)/6,$$

where a is the radius of the base of the spherical segment, h is the height of the spherical segment, and ρ is the density. For a contact angle θ of 60 degrees (h/a=0.578), a density of 0.81 gm/cc, and (a) measured in centimeters, the final expression for the mass of the droplet reduces to:

$$\text{Mass} = 0.82a^3 \text{ gms}.$$

It is noted that the equations above would slightly vary depending on the materials you are detecting. Here, we are assuming a contact angle θ of 60 degrees, for detection of hydrocarbon residue. The formulas described are extendable to measuring silicone oils and outgassing from gaskets and other disk drive components.

A conversion chart is provided, based on the formulas above and illustrated in connection with FIG. 5*b*, that converts the diameters measured into micrograms of the droplets. An example of such a conversion chart is illustrated in Table 1 below:

TABLE 1

Diameter Conversion to Weight of Droplets in Micrograms

| SCALE | AVG. WT | SCALE | AVG. WT |
|---|---|---|---|
| 1 | 0.0014 | 17 | 6.96 |
| 2 | 0.011 | 18 | 8.26 |
| 3 | 0.038 | 19 | 9.72 |
| 4 | 0.091 | 20 | 11.3 |
| 5 | 0.18 | 21 | 13.1 |
| 6 | 0.31 | 22 | 15.1 |
| 7 | 0.49 | 23 | 17.2 |
| 8 | 0.72 | 24 | 19.6 |
| 9 | 1.03 | 26 | 24.9 |
| 10 | 1.42 | 28 | 31.1 |
| 11 | 1.80 | 30 | 38 |
| 12 | 2.45 | 32 | 46 |
| 13 | 3.11 | 34 | 56 |
| 14 | 3.89 | 36 | 66 |
| 15 | 4.78 | 38 | 78 |
| 16 | 5.80 | 40 | 91 |

In one example, using Table 1 as provided above, the droplet diameter is measured at 16 reticule scale units and has an average weight of 5.80 µg, while a blank run droplet diameter of 8 scale units is measured at 0.72 µg. To find the weight of the sample, the blank weight is subtracted from the sample weight and rounded off to one decimal place. Now having the sample weight, the disk drive manufacturer can determine if the part is suitable for use in a disk drive system. FIG. 6*a* illustrates the relationship between the contact angle of a spherical segment of condensed material and the height to diameter ratio. FIG. 6*b* shows the ratio of the volume of a spherical segment with a fixed base diameter, normalized to the volume at a contact angle θ of 60 degrees, as a function of contact angle. Those skilled in the art appreciate that the contact angle will vary, either increasing or decreasing, based on the material being collected and the surface energy of the coating.

In a preferred embodiment, the lens 214 used in the method of the present invention is initially coated with a low surface energy coating liquid. The coating process is described as follows. First, the concave side of the lens 214 is cleaned with a solvent such as hexane. The lens 214 is then dried with filtered compressed air. This step also removes any fiber or debris from the lens. Next, one or two droplets of the coating liquid is placed on the concave side of the lens. The coating liquid should produce a coating with a surface energy lower than the liquid to be collected such that the liquid will not wet the surface. The visibility of the collected material is enhanced by a high contact angle of the liquid and the coated surface. The coating is rubbed repeatedly with a clean, lint free cloth until the liquid is distributed uniformly on the concave surface of the lens 214. Next, the lens 214 is placed on a hot plate and heated. The heating step may be for a minimum of 3 hours, but in a preferred embodiment, is closer to 12 hours. The lens 214 is then cooled to room temperature. If necessary, the lens 214 may be rubbed with a clean lintless cloth to remove any remaining residue. The lens 214 is suitable for use in the collection of organic materials.

In alternative embodiments, the lens 214 may be coated by other means such as dipping the lens in solution, or baking the lens 214 in an oven, without departing from the spirit or scope of the invention. Additionally, the low surface energy coating could be done by semiconductor processes such as sputtering or CVD.

FIG. 7 is a flow diagram of the steps in accordance with the method of the present invention, as used to measure the organic material on an actuator coil 46. Step 230 shows the collected organic material from the actuator coil on the surface of lens 214. Step 232 shows the addition of solvent to the collected organic materials. Next, step 234 shows the dissolution of the condensate into the solvent. Step 236 shows the evaporation of the solvent. Lastly, step 238 shows the concentrated organic material ready for microscope examination. For illustrative purpose, the parameters for an example in which the above described embodiment may be implemented effectively is set forth below. Given an single actuator coil, triangular in shape within a two inch diameter ring, the following parameters for the method described herein have been found to be effective:

(1) coating hotplate temperature: 145 degrees Celsius;

(2) heating time for coating step: 3 hours minimum, preferably 12 hours;

(3) cooling time for coating step: 30 minutes minimum;

(4) time for collection of condensible materials 10 minutes for standards, approximately 30 minutes for samples;

(5) hotplate temperature for collection of materials: 145 degrees Celsius;

(6) coating liquid for pretreatment of the lens is Z-dol. This is chosen as the coating liquid because it most conveniently provides a high contact angle surface required for the droplet diameter measurement step.

(The foregoing values are intended to provide an order of magnitude of the relative dimensions and parameters. Variations of these values can be made without departing from the implementation of the present invention.)

While the present invention has been particularly shown and described with reference to the illustrated embodiments thereof, it will be understood by those skilled in the art that various changes in form and detail may be made therein without departing from the spirit, scope and teaching of the invention. Accordingly, the invention herein disclosed is to be considered merely as illustrative and limited in scope only as specified in the appended claims. Although this invention describes the method and apparatus as applied to an actuator coil, it is obvious that and similar file components can be used and still maintain the spirit of this invention.

We claim:

1. A method for detecting organic materials on components used in a magnetic storage system comprising the steps of:

placing the component on a heat source;

covering the component with a concave lens having a low surface energy coating;

creating a temperature differential between the heat source and the concave lens;

vaporizing organic materials on the component, if any;

condensing the vaporized materials, if any on the concave lens;

collecting the condensate from the lens with a solvent droplet;

evaporating the solvent so that only a residue remains; and measuring the size of the residue.

2. The method as set forth in claim 1, wherein said step of creating a temperature differential is comprised of the steps of:

raising the temperature of the heat source; and maintaining a cooler temperature at the lens by use of a coolant.

3. The method as set forth in claim 2, wherein the temperature of the heat source is raised to about 145 degrees Celsius.

4. The method as set forth in claim 3, wherein the temperature of the lens is about 25 degrees Celsius in said maintaining step.

5. The method as set forth in claim 2, further including the step of coating the lens with a coating liquid prior to placing the lens over the component.

6. The method of claim 5, wherein said coating step is comprised of the following steps:

cleaning said lens;

applying a coating liquid onto the concave portion of said lens;

heating said lens and coating liquid until said coating liquid forms a thin layer on the lens held by adhesive forces;

cooling the lens to room temperature; and rubbing the surface to remove excess materials.

7. The method as set forth in claim 6, wherein the coating liquid is Z-dol.

8. The method as set forth in claim 7, wherein said lens and coating liquid is heated from 3 to 12 hours.

9. The method as set forth in claim 6, wherein said collecting step is comprised of the following steps:

dropping a droplet of a solvent on the concave portion of the lens, swirling said droplet over the lens to collect any residue of the condensate on the lens; and evaporating solvent from the droplet to provide a concentrated condensate material on said lens.

10. The method as set forth in claim 9, wherein the solvent is hexane.

11. The method as set forth in claim 9, wherein said measuring step is comprised of the following steps:

measuring diameter of the concentrated condensate material; and converting the diameter of the concentrated condensate material into weight of the concentrated condensate material.

12. The method as set forth in claim 11, wherein said component is an actuator coil.

13. The method as set forth in claim 11, wherein said component is a spindle motor winding.

14. The method as set forth in claim 11, wherein said component is a gasket.

* * * * *